(12) United States Patent
Pantino

(10) Patent No.: US 6,769,910 B1
(45) Date of Patent: Aug. 3, 2004

(54) METHODS AND APPARATUS FOR IMPROVED INTEROCCLUSAL MANDIBULAR REPOSITIONING WITH ADJUSTABLE RELATIONAL MEMBERS

(76) Inventor: Don A. Pantino, 4 Valley Ct., Mount Sinai, NY (US) 11766

( * ) Notice: Subject to any disclaimer, the term of this patent is extended or adjusted under 35 U.S.C. 154(b) by 0 days.

(21) Appl. No.: 09/392,999

(22) Filed: Sep. 9, 1999

(51) Int. Cl.$^7$ ................................................. A61C 3/00
(52) U.S. Cl. ............................................ 433/6; 433/19
(58) Field of Search ................................ 433/6, 18, 19, 433/24

(56) References Cited

U.S. PATENT DOCUMENTS

| | | | |
|---|---|---|---|
| 4,230,104 A | * 10/1980 | Richter | 433/19 X |
| 4,969,822 A | * 11/1990 | Summer | 433/19 |
| 5,842,856 A | * 12/1998 | Casey | 433/19 |

* cited by examiner

Primary Examiner—Nicholas D. Lucchesi

(57) ABSTRACT

A non-surgical oral appliance for improving breathing, and abating or completely alleviating snoring sounds, TMJ and bruxism while sleeping. In one embodiment the user is professionally fitted for the appliance such that the appliance positions the mandible in an open, protrusive, predetermined position such that the oral airway permits the enhanced passage of air. In another embodiment the user is "self" fitted and there in may customize the appliance in the home or like setting such that the appliance positions the mandible in an open, protrusive position such that the oral airway permits the enhanced passage of air. Either appliance embodiment may have either a bi-lateral attachment means or anterior means wherein each appliance may have upper and lower surfaces that cover and mold to the respective shape(s) and in contour with the user's teeth. Positioned upon these upper and lower surfaces, either bi-laterally or anteriorly, are attachment means. These attachment means are further positioned and adjusted to provide the optimum oral opening coupled with comfort.

16 Claims, 8 Drawing Sheets

Figure 1:
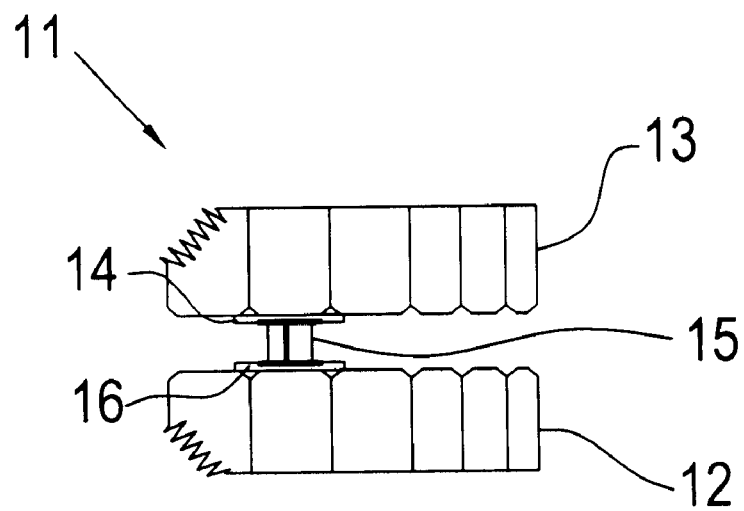

METHODS AND APPARATUS FOR IMPROVED INTEROCCLUSAL MANDIBULAR REPOSITIONING WITH ADJUSTABLE RELATIONAL MEMBERS

BACKGROUND OF THE INVENTION

The present disclosure relates to improved methods and apparatus for use in mandibular repositioning. More particularly, the present inventions relate to creating a custom fitted mandibular repositioning appliance that is easily adjustable and customized while reducing tissue impingement that may otherwise compromise airway space and/or architecture. The inventions' consist of manners of attachment situated between the mandible and maxillary bite block or occlusal plains permitting structural stability and integrity allowing for user comfort and mobility as never before addressed or available. Furthermore, the attachment means element allows for infinite horizontal and vertical adjustability within the dimensions of the appliance and its attachment means. The novelty of this invention stems from the attachment means used and the location thereof.

The inventions relate to therapy in the treatment of sleep apnea, snoring, bruxism, and other now known or future diagnosed oral, respiratory, dental and developmental disorders that may affects the dentition and surrounding skeletal and muscular structures. In particular, the present inventions relate to improved methods and apparatus for enhanced precision and control of interocclusal devices used in patient therapy.

Difficulty in breathing while sleeping often manifests itself as snoring or the more serious obstructive sleep apnea. Snoring is a condition affecting approximately forty percent (40%) of the adult population, while sleep apnea is believed to affect at least twenty (20) million people.

In turn, bruxism consists of a static and/or dynamic contact between the dentition of the mandible and maxilla. Bruxism is commonly referred to as "tooth grinding" which results in the physical destruction of tooth enamel directly leading to tooth decay as well as more serious problems. Bruxism affects nearly fifteen percent (15%) of the population and in advanced stages bruxism results in the abnormal and excessive grinding or clenching of teeth while an individual is asleep. Bruxism is medically classified as parasomnia or sleep disorder. In some instances a person may be so unaware of the problem that it may occur while awake. As the individual may not be conscious of the problem, if bruxism becomes a habit it may become even more difficult to treat.

The actual cause of bruxism is not clear, however reference has been made to causes being related to emotional stress or other psychological factors. Common treatments range from psychotherapy, sedatives or tranquilizers and may further include bio-feedback, i.e. electrodes being taped to the jaw.

In turn, temporomandibular joint syndrome (or dysfunction) ("TMJ") is a disorder effecting the joint between the lower jaw and the skull. The temporomandibular joint lies between the temporal bone of the skull and the mandible of the jaw, and allows the jaw to open and close. The joint is formed by a condyle on the mandible which hinges and glides in and out of the depression in the temporal bone.

TMJ can be caused by bruxism, malocclusion, trauma, and arthritis. There is also an indication that a posterior or backward displacement of the condyle of the jaw significantly contributes to TMJ pain. TMJ has been associated with a wide variety of physical aliments, including migraine headaches. TMJ related headaches can become so severe as to cause nausea and blurred vision. Most people afflicted with TMJ suffer from a myo-facial pain-dysfunction syndrome primarily as a muscle problem related to dental/skeletal relationships and tensional factors. The effects can range from mild to severe, including pain in the joint area that can extend to the shoulders, back, neck, and sinuses. As a treatment, surgery is only utilized in the most severe cases, which represent approximately ten percent (10%) of those seeking treatment.

Accordingly, the medical profession and related health care industries have now begun to recognize the paramount importance of developing new and innovative techniques that effectively address one (1) or all of the aforementioned maladies. Therein, oral appliances (interocclusal devices) have been employed to prevent the tongue and/or collapse of oral pharyngeal tissue from obstructing the airway. To date, when used in the treatment of snoring or sleep apnea, these prior techniques and devices have been either unsuccessful, met with limited success or have resulted in undesirable side effect(s).

In a paper entitled *Dental Appliances for the Treatment of Snoring and/or Obstructive Sleep Apnea*, by Alan A. Lowe published in *Principles and Practice of Sleep Medicine*, W. B. Saunders Company, Second Edition 1994, chapter 69, pp. 772–785, a number of commercially available or experimental devices known were described together with their inherent problems and advantages. Most of these devices manipulate the tongue or adjust the relative positions of the mandible to the upper jaw. The latter being more desirable because the less the tissue contact, the less the tissue irritation and damage.

Tongue devices such as U.S. Pat. No. 4,715,368, and Reissue No: 33,442, issued to George discloses an oral device preventing the closure of the breathing passage. The George device uses flanges to depress and constrain the tongue.

U.S. Pat. No. 3,132,647, to Corniello teaches keeping the air passage open by engaging and depressing the rear portion of the tongue while supporting a portion of the downwardly hanging soft palate. The Corniello device resembles the :upper portion of an athletic mouth guard, with a metal tongue depressor at the back.

U.S. Pat. No. 4,169,473, to Samelson describes a device for positioning within the mouth of a user to prevent snoring and nocturnal bruxism. The Samelson device has an integrally molded body providing dental engaging arches and a rearwardly-opening central socket for cooperating with the forward portion of the user's tongue in a manner which draws the tongue forward in order to increase the oral-pharyngeal airway space.

U.S. Pat. No. 3,434,470, to Strickland functions to control the amount of air capable of passing through the mouth, either lessening the intake volume of air to an extent wherein the person is incapable of producing a snore, or shutting off completely the passage of air through the mouth. The limitations with these types of devices are in restriction of airflow, impedance and limited or hindered tongue mobility, and thus tend to interfere with normal swallowing patterns. Importantly, constraint(s) placed upon the tongue tends to be uncomfortable and thus discourage use, resulting in decreased patient use and limited effectiveness.

Conversely, the Herbst appliance is an oral device that attempted to realign the mandible and maxilla. The Herbst appliance, which is shown in German Patent No. 374,163, consists of a metal band placed around an upper molar and lower incisor tooth. The two (2) bands are interconnected by a telescopic member and exert an anteriorly directed force on the mandible. This device needs great strength to resist "breakage" from lateral jaw forces. Whereas, another Herbst appliance uses retentive blocks rather than banding directly to teeth.

Other, similar telescopic devices include those shown in U.S. Pat. No. 3,618,214, to Armstrong, as well as many other similar patents. All of these devices teach required wires or braces for attachment to the patient's teeth.

U.S. Pat. No. 4,901,737, issued to Toone exemplifies the prior devices. Toone discloses an intra-oral appliance for reducing snoring which repositions the mandible in an open and protrusive position as compared to the normally closed position of the jaw. The Toone appliance includes a pair of V-shaped spacer members formed from dental acrylic which extend between the maxilla an mandible to form a unitary mouthpiece.

U.S. Pat. No. 1,674,336, to King teaches an appliance for placement between the teeth of the user. The King device resembles an athletic mouth guard, and has upper and lower channels which receive the upper and lower teeth respectively. The channels are spaced apart so there is a central air passage between them. In use, the King device moves the lower jaw downward, not forward, and forward is the preferred placement of the mandible in relation to the maxilla.

In U.S. Pat. No. 5,365,945, issued to Halstrom an attempt was made at allowing for a limited degree of lateral movement. The device contained only one (1) point of attachment. Due to the size, location, and surrounding supportive material necessary to maintain the attachment means fixed in this implementation, the device impinges tongue space due to the frontal point of attachment and as a proximate result the airway architecture is altered.

U.S. Pat. No. 5,066,226, issued to Summer is comprised of a bi-lateral "spring-like" means for attachment. Finally, U.S. Pat. No. 5,409,017, issued to Lowe discloses a double threaded attachment means located in the palate area.

In turn, the inventions as disclosed in this application, and in its additional embodiments, proposes a much more compact and precise attachment means, thereby more effectively alleviating problems. Furthermore, the "micro" scaling, the strength of titanium coupled with its novel designs, infinite adjustability over a range, lateral and protrusive adjustment overcomes the inadequacies of the other devices.

In conclusion, the prior devices' shortcomings range from: 1) limited or no adjustability; 2) tissue impingement and irritation; 3) serious and or significant impingement of tongue space; 4) significantly or severely altering the airway's architecture; 5) minimal patient comfort; 6) bulkiness; 7) little or no free range of motion, and 8) only minimally addressing and remedying that for which they were intended.

In turn, aside from professional "custom" manufacture there is a need for "mass-produced" oral devices such that the costs associated with specific professional services directed to an individual user may be minimized while accomplishing the same goals and objectives addressed herein.

Therein, a means to achieve mass production include the ability for the user to adjust the mandible protrusion themselves and create their own custom formable mouthpiece through the use of a thermoplastic or similar material as described herein with or without the aid of a physician. Their exists several prior references which allude to the use of a formable thermoplastic or such polymeric material mouthpiece or mouth guard however fail to include operative means for mandibular protrusion. Accordingly, the following is a review of some oral devices potentially capable of being "mass produced".

U.S. Pat. No. 5,031,638, issued to Castaldi, teaches a mouthguard formed from a blank which includes an inner layer, rigid core disposed adjacent to and coextensively with the core. Impressions of the user's dentition are made in the inner and outer layers by heating the blank to a predetermined temperature range and subjecting the blank to bit pressure. The impressions are set and the finished mouthguard is formed by cooling the blank below the predetermined temperature range. The core is formed from a material having a softening temperature above the predetermined temperature range and therefore provides structural support for the inner and outer layers when the blank is heated to the predetermined temperature range and after the blank is cooled to form the finished mouthguard.

U.S. Pat. No. 5,152,301, issued to Kittelsen, et al., discloses a thermoplastic mouthguard having a "U-shaped" base with top and bottom side and upward inner lingual and outer labial walls forming a channel for the maxilla having posterior and anterior portions. Occlusal posterior pads are on the bottom side of the base along the posterior portions of the guard to space apart the anterior teeth of the lower jaw from the anterior portion of the bottom side of the "U-shaped" base and to lessen pressure and possible impact forces. A rigid framework tray is provided for assisting in heating the mouthguard and positioning and aligning the mouthguard for custom formation to the user's mouth.

U.S. Pat. No. 5,339,832, issued to Kittelsen, et al., teaches a composite mouthguard having a flexible and tough, softenable thermoplastic mouthguard portion with a "U-shaped" base having upward inner lingual and outer labial walls extending from the base. A shock absorbing and attenuating non-softening, resilient, low compression, elastomer framework is embedded in the mouthguard portion to absorb, attenuate and dissipate shock forces exerted on the mouthguard during athletic activity.

U.S. Pat. No. 5,746,221, issued to Jones, et al., discloses a cold formable mouthguard that provides protection to the teeth, gums, jaw, and joints of the facial region to absorb and dissipate energy and thus minimizing further injuries. The mouthguard can be shaped to retain the contours of the teeth and mouth by simply placing the mouthguard into the mouth and biting down, without the need for first boiling to soften or other such shaping step.

These references all teach the use of a thermoplastic or other such polymeric material which may be custom molded by the user, but none teach or imply their use in the treatment of any type of oral, dental, maxillo-facial, pharyngeal, or other such disease or malady.

The need has therefore arisen for a dental appliance that treats the aforementioned maladies that may be custom manufactured or mass produced by which either embodiment is capable of maintaining the mandible in a preferred protruded position, while allowing for a limited degree of lateral and protrusive movement thus minimizing the negative effects of a static positioning of the: 1) teeth and related muscles and ligaments; 2) temporomandibular joint irritation or aggravation; 3) decreased impingement or disruption of tongue airway/architecture and flow, individually and in combination, and 4) rigid fixation of teeth to limit tooth movement and undesirable occlusal change. These and other objects and advantages of the present invention will become apparent from the following description and by reference to the accompanying drawings.

SUMMARY OF THE INVENTION

Methods and devices that allow for articulation and disarticulation and positioning of the mandible in relation to the maxilla is disclosed. Such movement and ranges of motion coupled with the unique and novel manners of attachment between the upper and lower relational members allow precise control of mandibular placement. Further, the precise positioning allows for a range of motion in static and functional use. Additionally, the ability to articulate and disarticulate allows for comfort in insertion and application in the patient's mouth and allowing for divergent paths of insertion and withdrawal between the invention's means for articulation. The device provides for infinite adjustability within the dimensions of the oral cavity.

What is disclosed are methods and devices that allow for the mandible to be retained in a position, determined by the physician, dentist, or like professional, in relation to the maxilla. Such mandibular positioning reduces the possibility of the airway collapsing and thus the related breathing disorders. In addition, fixation of the mandible is effective in reducing or eliminating the symptoms arising from bruxism and TMJ.

Disclosed herein are methods and devices that allow for the reduction of impingement of tongue and airway's architecture. Additionally, the alleviation of tongue contact is established by means of either bi-lateral points of attachment or and anterior point of attachment placed interocclusally in either embodiment between the respective upper and lower bite block or occlusal plains. Furthermore, the ability to position the attachment means interocclusally avoids tongue crowding that has a direct negative effect upon the airways architecture directly resulting from the tongues "unnatural" or altered positioning and/or posturing.

What is also disclosed are devices that allow for the opening of the oral airway in a manner comparable to auto-titration as described in CPAP and similar devices. This is accomplished by providing a limited range of protrusive movement while keeping the mandible and maxilla in a relative fixed position.

What is disclosed are methods and devices for treating snoring, obstructive sleep apnea and other afflictions by adjustably maintaining a patient's mandible in a preferred position comprising the steps of, for example in several embodiment: 1)once the dentist or physician determines the therapeutic position for a particular patient, an appropriate mold is taken of the maxillary dentition and of the mandibular dentition for formation of the appliance template; 2) securing a first attachment means to the undersurface of the template's upper bite block or occlusal plain, the first attachment means comprised of a series of means to accept and maintain an attachment element attached thereto; 3) securing or molding a second attachment means to an upper surface of the template's lower bite block or occlusal plain, the second attachment means comprising an area to accept and maintain an attachment element within a cavity of the second attachment means, 4) determining the preferred degree of mandibular protrusion or positioning required to alleviate the patient's maladies, and 5) affixing the relational members in said protrusion or position.

According to the principles disclosed herein are fitted and infinitely adjustable oral appliances for improving sleep disordered breathing and for the reduction of other maladies with a structural shell comprised of durable, light weight, semi-rigid, formable material. The structural shell will comprise opposed upper and lower members. In turn, in the embodiments each member has attachment means, affixed, attached or molded, on either its respective adjacent sides on opposing upper and lower surfaces of the bite block or occlusal plain. And in another embodiment, the anterior region of the upper and lower members, on opposing upper and lower surfaces of the bite block or occlusal plain. The attachment means is located on the surface directly above the crown of the tooth beneath the member such that the attachment means is affixed, molded or otherwise attached to or on the opposing bite block or occlusal plains, i.e., the upper and lower members. (Envision the surfaces of upper and lower teeth directly opposing each other. Therein there is a surface contact area between the teeth that when the teeth are in contact with each other would constitute the bite, now just expanded opposing teeth to multiple teeth and there is a "bite block or occlusal plain". Now envision a manner for connecting the bite block or occlusal plains when they are not in direct contact with each other and then "insert" a means for attachment or maintain a predetermined distance a relative constant, hence the attachment element.). The upper member, with respective attachment means, appropriately positioned, either bi-laterally or anteriorly, will in turn have an attachment element structurally affixed to it so as to allow for the upper members attachment to the lower member. The lower member is also comprised of an attachments means, appropriately positioned, either laterally or anteriorly, whereby an attachment means allows for initial attachment of the attachment element opening the airway and thus increasing the vertical position of the hyoid bone and therefore further effecting and optimizing the airway. Then upon advancing of the mandible the device is articulated, thus allowing lateral movement in its articulated position. In turn, a complete appliance, by ways of the attachment element and means, outwardly advances or positions the mandible forward with respect to the maxilla and by way of the positioning of the attachment means, either bi-laterally and posteriorly, or anteriorly, there is minimal impediment of the tongue or oral architecture as never before available.

The upper and lower members of the structural shell are molded from a dental impression and then appropriately fitted and adjusted for a custom fit. The members are preferably formed of flexite or other similar material. The material, e.g., flexite, presently available allows for the structural shell to be comprised of a more durable material able to sustain its structural integrity under the physical and chemical forces of the mouth, as never before possible. In turn, allowing for the equal distribution of lateral and vertical forces and minimum tissue or oral airway impingement due to the physical properties of the material and appliances' design. In an alternate embodiment using user adjustable attachment means, said molds may be comprised of a material of similar properties as described above which may be custom cast or molded by the user in his or her own home. The shell may be created by injection mold processes, cold casting, or other like means known by those skilled in art with the attachment means "pre-cast", "pre-molded" or "pre-affixed" for home use and modification. Such an embodiment allows for mass production and distribution of a "universal" snore reduction device.

The attachment means of the upper member is attached, molded, affixed or otherwise secured to or on the structural shell in the area that is otherwise "covering" the top or crown of the tooth or teeth, e.g., the opposing surface(s) of the bite block or occlusal plains, thus allowing for interocclusally, structurally sound and durable positioning. The attachment means are comprised of titanium or other material with similar properties. The attachment means may contain a beveled edge, allowing for its recessing into the upper member. The upper attachment means, in either the anterior or bi-lateral embodiment, may consists of track-like means having a recessed retaining nut or like retention means or attachment means molded directly into the member. The track allows the attending physician, dentist, like professional or individual to determine and fixedly position, non-discretely, any amount of mandible protrusion by the tightening of the attachment element into the retaining nut within the confines of the track-like means. Attached to the retaining nut is a screw or other attachment element comprised of titanium or like material. The head of the screw may be flat or concave at its distal end. The shaft may be completely threaded or otherwise. Alternatively, the attachment element may be comprised of two (2) flat head or concave surfaces connected by a shaft. Said screw or other attachment element mates with the lower attachment means. Additional manners and apparatuses may be utilized to accomplish the same and inasmuch will become obvious to one skilled in the art upon review of this disclosure.

The attachment means of the lower member(s) is attached, molded, affixed or otherwise integrated and secured to the structural shell thus allowing for structurally sound and durable positioning to or on the structural shell in the area that is otherwise "covering" the top or crown of the tooth/ teeth, e.g., the opposing surfaces of the bite block or occlusal plains. The attachment means are comprised of titanium or other material with similar properties. The attachment means of the lower member comprises an opening or hole-like area that may or may not be threaded or other attachment components that allows for the positional attachment, movement and placement of an attachment element. The lower attachment means, in either the anterior or bi-lateral configuration, could consist of a track of lesser width than the head of the screw or other such attachment element. Said track features ample diameter to accept the head of the attachment element for initial attachment and then disarticulation of the oral appliance. The hole also comprises an area through which the shaft of the attachment element may pass. The hole also comprises an area where in the shaft may move laterally without the head passing therethrough during the oral appliance's articulation. The hole has a beveled inside edge thus allowing for the head to the attachment element to slide or otherwise pass within the confines of the attachment means. Such mating mechanism can be alluded to a chain lock on a door. The length of the track on said lower attachment means allows the user some freedom in mandible protrusion with respect to the maxilla, but is limited by the fixed position of the retaining nut in said upper attachment means. Limited lateral movement of the mandible relative to the maxilla is possible due to the track in said lower attachment means having a width slightly greater than that of said screw's or other attachment element's shaft diameter.

Said anterior connecting means arrangement includes two embodiments. In one embodiment, said connecting means are oriented latitudinally. Such arrangement allows the attending dentist, physician, like professional or individual to fix lateral movement of the mandible, while allowing limited mandibular protrusion. This embodiment is useful in the treatment of bruxism and the other aforementioned maladies.

In another embodiment, said connecting means may be oriented longitudinally. Such arrangement allows the attending dentist or physician to fix mandibular protrusion, while allowing limited lateral movement of the mandible. This embodiment is useful in the treatment of snoring, sleep apnea, and other mentioned sleep disorders and maladies. In both embodiments, connecting means are located interocclusally on the opposing surface of the respective bite block or occlusal plains.

When the device is used and in position, the device provides necessary protrusive jaw movement sufficient to open the airway and eliminate snoring sounds. Additionally, the device provides an opening between the mandible and maxilla to permit an adequate airway.

Many other advantages and features of the present invention will become obvious to those familiar in the art with review and reference to the detailed description and accompanying drawings.

Thus, it is an object of the present invention to provide a interocclusal repositioning appliance that may be is custom or mass produced and therein fitted and easily adjustable for the treatment of sleep disordered breathing, bruxism etc., and other above mentioned maladies and afflictions.

Another object of the invention is to provide for a protrusive infinitely adjustable oral appliance within the dimensions of the oral cavity.

Yet another object of the invention is to provide for a vertically infinitely adjustable oral appliance within the dimensions of the oral cavity.

Another object of the invention is to provide a device of the type described which does not cause discomfort to the user or harm to the teeth, tongue, temporomandibular joint or gums during use.

Another object of the invention to provide an improved oral cavity device that can be used by persons to give relief from snoring and sleep apnea, and that provides for breathing through the mouth, nares or both.

Still another object of the invention is to provide a device of the type described which is of durable and reliable construction since therapy may be required for life.

Yet another object of the invention is to avoid and minimize alteration of the oral airways architecture.

Another object of the invention is to provide a device that minimizes, alleviates or eliminates tongue irritation or contact with an oral appliance or parts thereof.

Another object of the invention is to reduce or eliminate the impingement upon tongue space.

Another object of the invention is to aid in the treatment of TMJ disorders.

Still another object of the invention is to reduce or eliminate bruxism and its negative effects.

Another object of the invention is to permit for a range of protrusive motion to aid in swallowing.

Another object of the invention is to permit for a range of lateral motion.

Another object of the invention is to reduce or eliminate the impingement upon vestibular space.

Yet another object of the invention is to allow for infinite adjustability with in the confines of the device's parameters.

Another object of the invention is to allow for precision placement of the mandible in relation to the maxilla.

These and other objects and advantages of the present invention will become apparent from the following description and by reference to the accompanying drawings.

BRIEF DESCRIPTION OF THE DRAWING FIGURES

FIG. 1. FIG. 1 depicts an angulated lateral view of the bi-lateral attachment embodiment(s).

Figure 2:
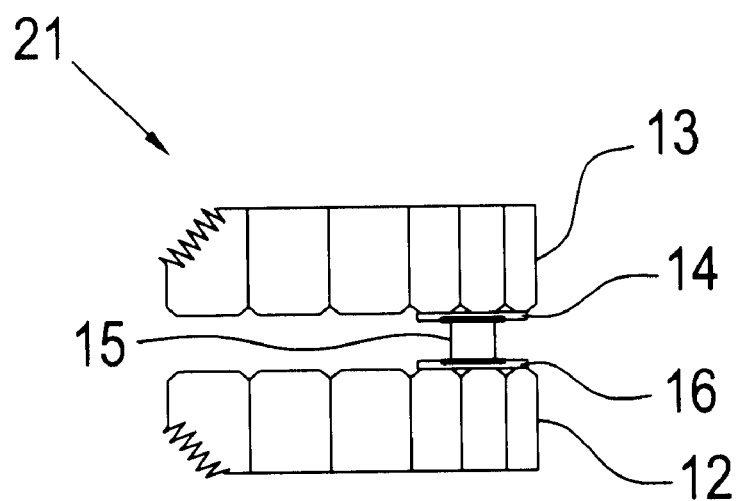

FIG. 2. FIG. 2 depicts an angulated lateral view of the anteriorly located, longitudinally oriented attachment means embodiment(s).

Figure 3:
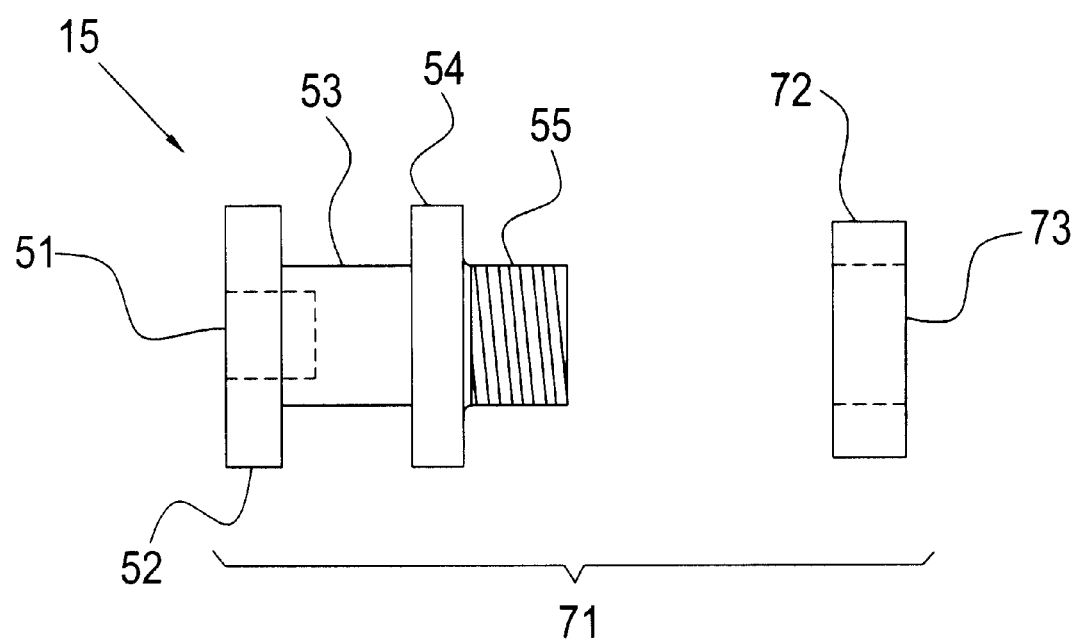

FIG. 3. FIG. 3 depicts a possible attachment element along with a retaining nut.

Figure 4:
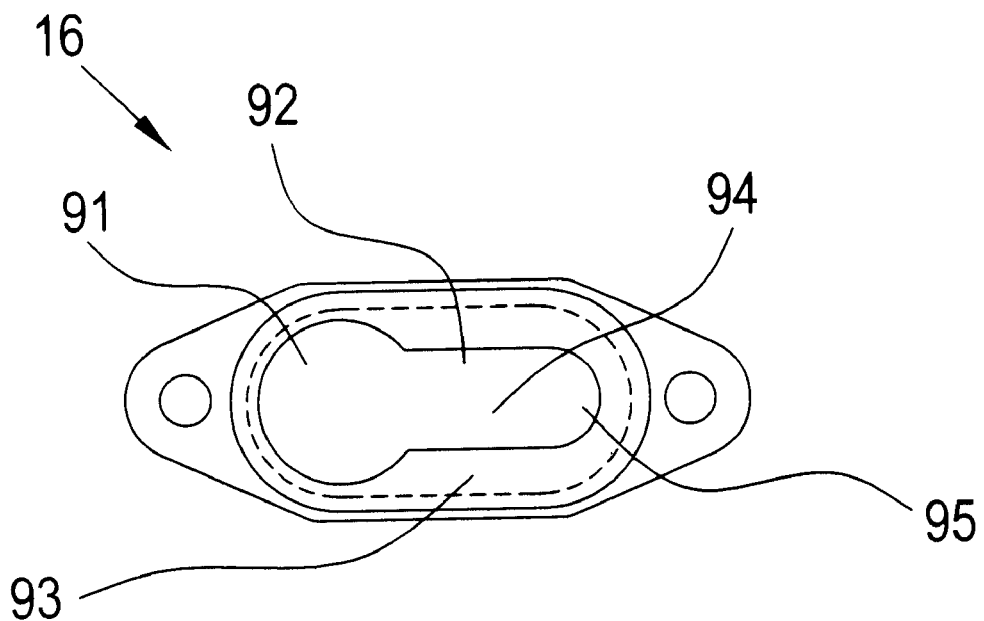

FIG. 4. FIG. 4 depicts a view of the invention's lower bi-lateral and anterior longitudinally oriented attachment means.

Figure 5:
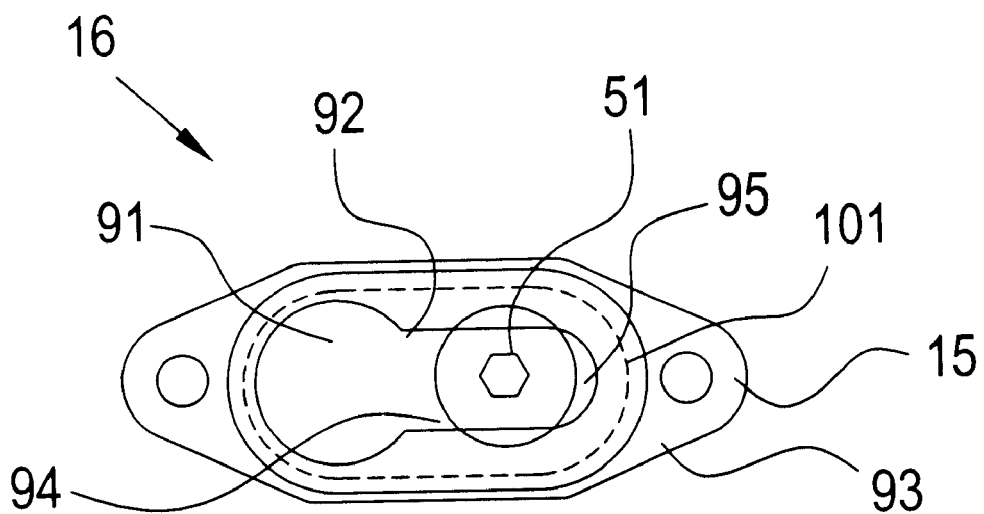

FIG. 5. FIG. 5 depicts a view of the invention's lower bi-lateral and anterior longitudinally oriented attachment means with a screw overlay.

Figure 6:
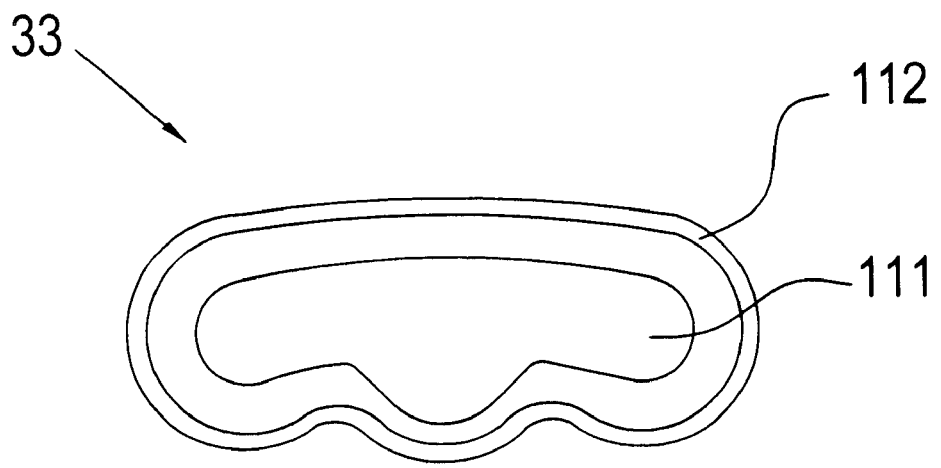

FIG. 6. FIG. 6 depicts a view of the invention's lower anteriorly located, latitudinally oriented attachment means.

Figure 7:
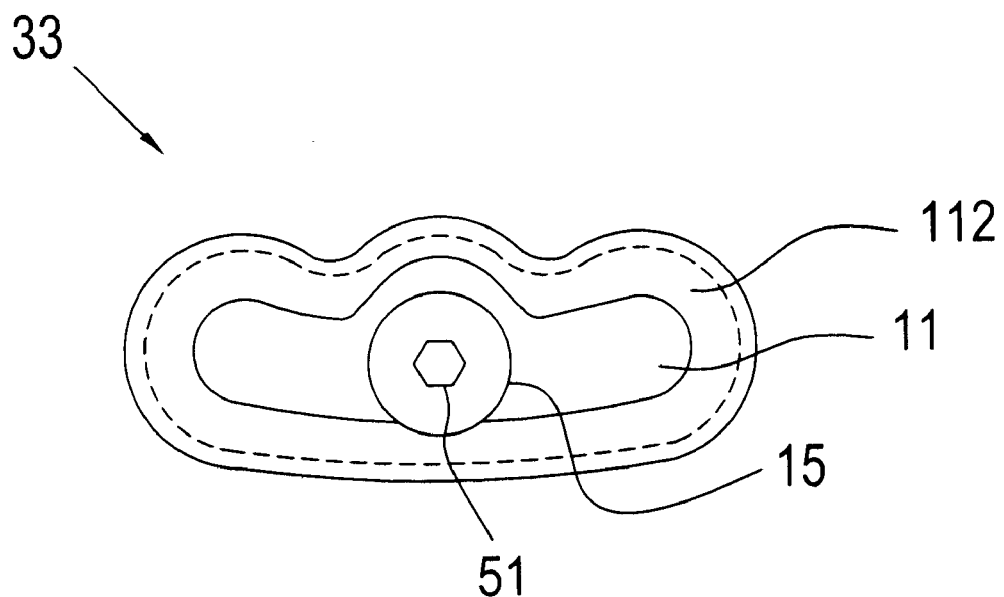

FIG. 7. FIG. 7 depicts a view of the invention's lower anteriorly located, latitudinally oriented attachment means with a screw overlay.

Figure 8:
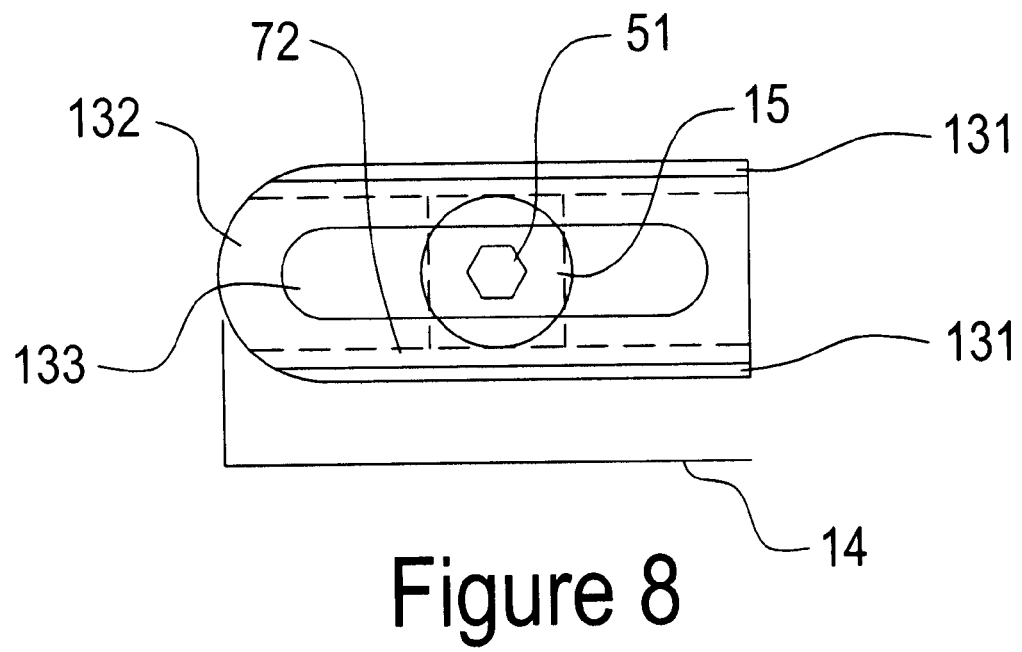

FIG. 8. FIG. 8 depicts the exposed view of the invention's upper attachment means.

Figure 9:
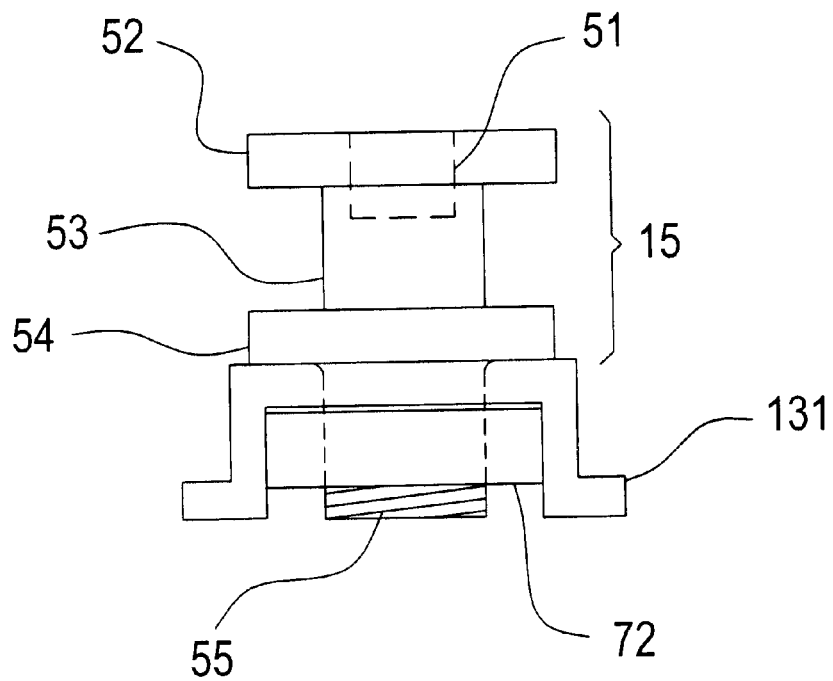

FIG. 9. FIG. 9 depicts a side view of the invention's upper attachment means.

Figure 10:
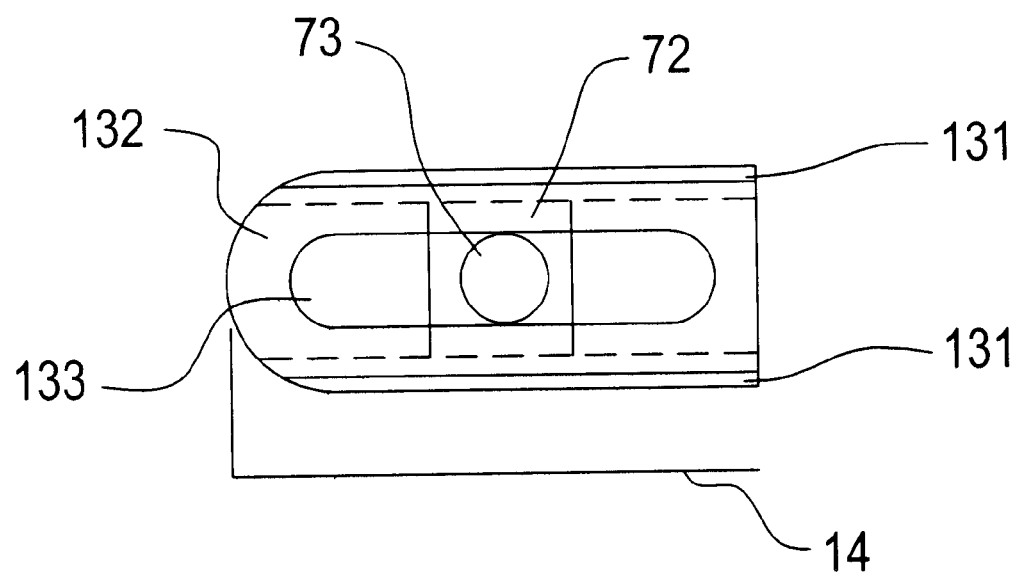

FIG. 10. FIG. 10 depicts another exposed view of the invention's upper attachment means.

Figure 11:
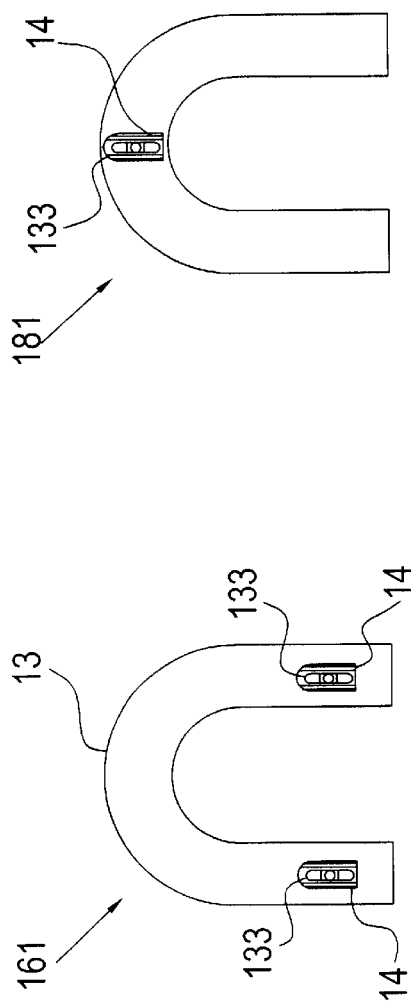

FIG. 11. FIG. 11 depicts an upper member and upper attachment means in a bilateral embodiment.

Figure 12:
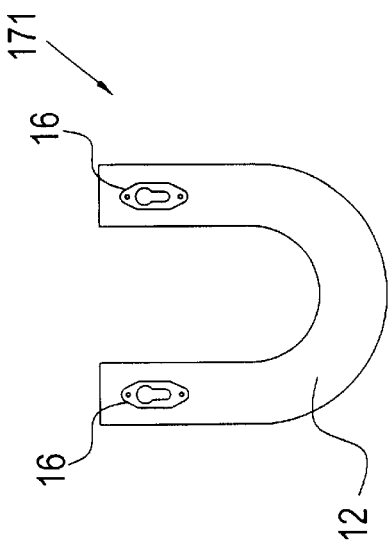

FIG. 12. FIG. 12 depicts a lower member and lower attachment means in a bi-lateral embodiment.

Figure 13:
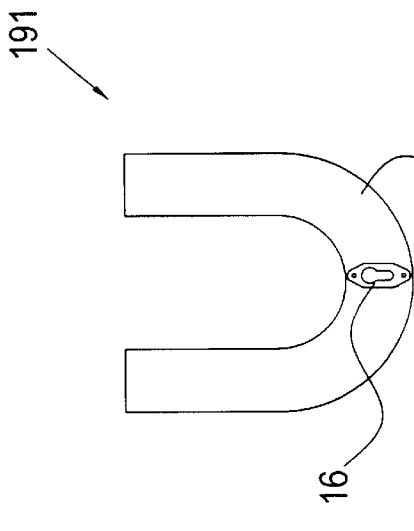

FIG. 13. FIG. 13 depicts an upper member and upper attachment means in the anteriorly located, longitudinally oriented embodiment.

Figure 14:
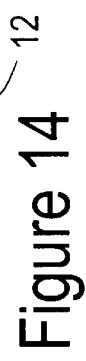

FIG. 14. FIG. 14 depicts a lower member and lower attachment means in the anteriorly located, longitudinally oriented embodiment.

Figure 15:
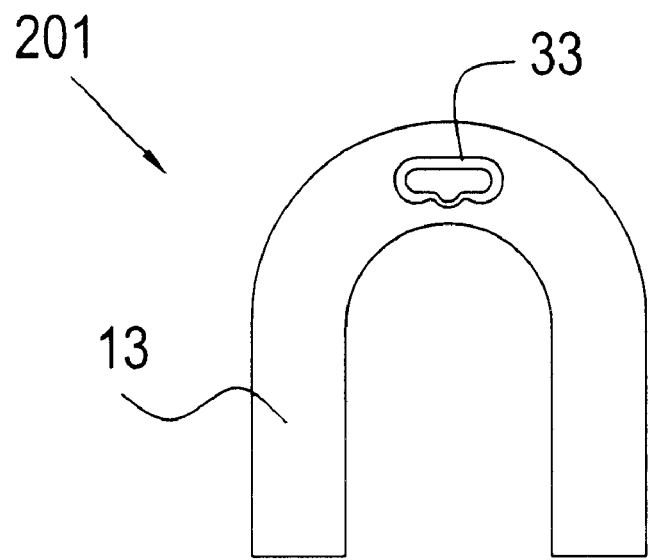

FIG. 15. FIG. 15 depicts an upper member and upper attachment means as used in an anteriorly located, latitudinally oriented embodiment.

Figure 16:
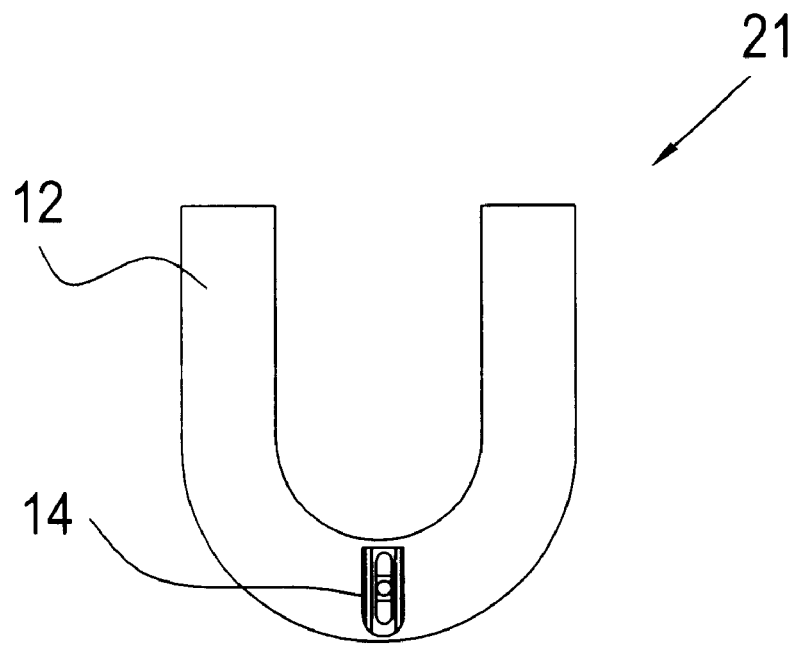

FIG. 16. FIG. 16 depicts a lower member and lower attachment means in an anteriorly located, latitudinally oriented embodiment.

Figure 17:
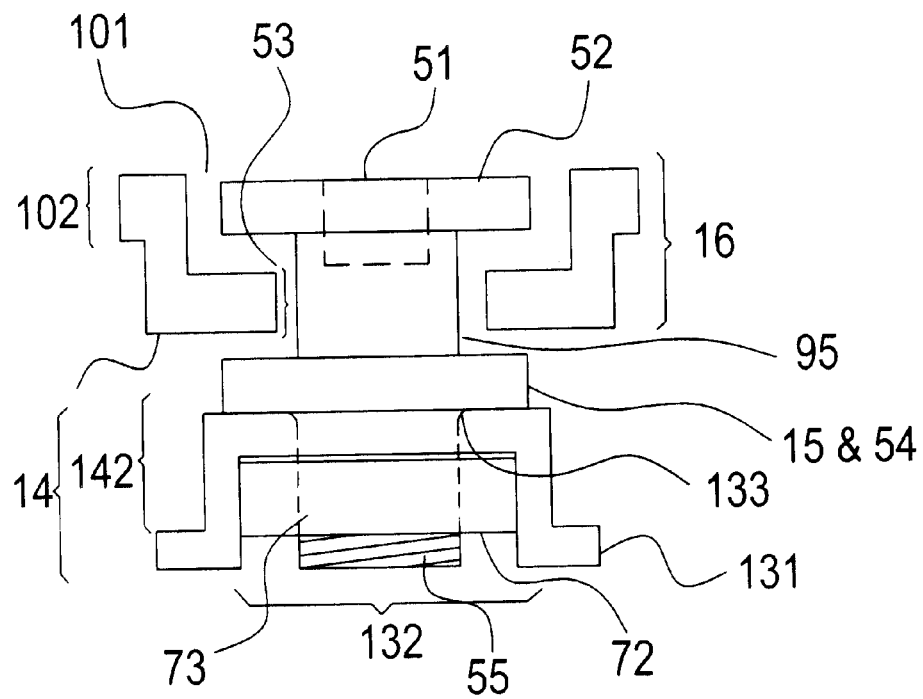

FIG. 17. FIG. 17 depicts a cross section of a longitudinal upper attachment means articulated with the longitudinal lower attachment means.

DETAILED DESCRIPTION OF THE PREFERRED EMBODIMENTS

FIG. 1. FIG. 1 depicts a profile of a custom fitted and manufactured oral appliance 11 that is constructed of a material capable of withstanding the physical and chemical stresses exerted from placement and usage in the mouth while capable of customization to the user's specific anatomical features, e.g., flexite. In this diagram, a bi-lateral embodiment is depicted, consisting of upper attachment means 14 that may be "pre-cast", "pre-molded", "pre-affixed" or alternatively cast, molded or affixed by the attending professional, attachment elements 71, and lower attachment means 16 that may be pre-cast, pre-molded or pre-affixed or alternatively cast, molded or affixed by the attending professional. The attachment means 14, 16 are on what would be the area of the upper and lower members 13, 12 in the areas that would be directly above or on top of the crown(s) of the tooth (teeth) otherwise known as the bite block or occlusal plain. The upper and lower members 13, 12 are of a minimal thickness such that air flow and the oral architecture are minimally impinged but thick enough to allow for the attachment, molding, casting or insertion of the attachment means 14, 16. The upper member 13 is molded, custom or otherwise derived, from a maxillary impression. The lower member 12 is molded, custom or otherwise derived, from a mandibular impression. Upper member 13 has an attachment means 14 on both respective adjacent sides of said member. Said attachment means 14 in turn have attachment elements 71, consisting of various parts 15, 72, connected or attached thereto. In turn, lower member 12 has an attachment means 16 on the respective adjacent sides of said member. Said attachment means 16 in turn have said attachment elements 71 connected or attached thereto.

In an alternative embodiment FIG. 1 may depict a profile of a mass produced, fitted oral appliance 11 that is constructed of a material that is capable of withstanding the physical and chemical stresses exerted from placement and usage in the mouth while capable of being customized to the user's specific anatomical features with the same being done by the user. In this embodiment, a bi-lateral embodiment is depicted, consisting of upper attachment means 14 that may be pre-cast, pre-molded or pre-attached, attachment elements 71 and lower attachment means 16 that may be pre-cast, pre-molded or pre-attached. The attachment means 14, 16 are on what would be the area of the upper and lower members 13, 12 in the areas that would be directly above or otherwise on top of the crown(s) of the tooth (teeth) otherwise known as the bite block or occlusal plain. The upper and lower members 13, 12 are of a minimal thickness such that air flow and the oral architecture are minimally impinged but thick enough to allow for the attachment, molding, or insertion of the attachment means 14, 16. The upper member 13 is molded, custom or otherwise, from a maxillary impression. The lower member 12 is molded, custom or otherwise derived, from a mandibular impression. Upper member 13 has secured thereto an attachment means 14 on both adjacent sides of said mold. Said attachment means 14 in turn have attachment elements 71, consisting of various parts 15, 72 connected or attached thereto. In turn, lower member 12 has an attachment means 16 on both adjacent sides of said member. Said attachment means 16 in turn have said attachment elements 71 connected or attached thereto.

In yet another embodiment, FIG. 1 may depict a profile of a custom fitted, manufactured and produced oral appliance 11 or alternatively mass produced either, one of which may be constructed of material(s).that is(are) capable of withstanding the physical and chemical stresses exerted from placement and usage in the mouth while capable of customization to the user's specific anatomical features. In this diagram, a bi-lateral embodiment is depicted, consisting of upper attachment area (otherwise representatively depicted as 14), attachment elements 71, and lower attachment area (otherwise representatively depicted as 16). The attachment areas (representatively depicted as 14, 16) are in the area of the upper and lower members 13, 12 that would be directly above or on top of the crown(s) of the tooth (teeth) otherwise known as the bite block or occlusal plain. The upper and lower members 13, 12 are of a minimal thickness such that air flow and the oral architecture are minimally impinged but thick enough to allow for the molding of the attachment area (representatively depicted as 14, 16). The upper member 13 is molded, custom or otherwise derived from a maxillary impression. The lower member 12 is molded, custom or otherwise derived from a mandibular impression.

Upper member 13 has an area molded for the attachment of the attachment element 71 to be secured thereto (the area is representatively depicted as 14) on both adjacent sides of said member. In turn, attachment elements 71 consists of various parts 15, 72 connected or attached thereto. In turn, lower member 12 has an area molded for the attachment of the attachment elements 71 to be secured thereto (the area is representatively depicted as 16) on both adjacent sides of said member.

The areas on the upper 13 member (representatively depicted as 14) would have an attachment means for attachment to the attachment element 71 with a retaining nut 72 affixed or otherwise placed therein. The area (representatively depicted as 14) is in what would be the area of the upper member 13 that would be directly above or on top of the respective crown(s) of the tooth (teeth) otherwise known as the bite block or occlusal plain. The upper members 13 are of a minimal thickness such that air flow and the oral architecture are minimally impinged but thick enough to allow for the molding of the attachment means (representatively depicted as 14). The attachment means (representatively depicted as 14) may be, in one embodiment, comprised of an opening and a track-like means in which a recessed retaining nut (i.e., 72) may be located within the track-like means. The nut (i.e., 72) is free to move within the confines of the track but may be fixedly connected or adjustable so that rotation is not possible. The attachment area (representatively depicted as 14) may be molded into or on the upper member 13 such that a sound and durable manner of affixation may be obtained.

The areas on the lower 12 member (representatively depicted as 16) would have an attachment means for attachment to the attachment element 15. The areas (representatively depicted as 16) are in what would be the area of the lower members 12 that would be directly above or on top of the respective crown(s) of the tooth (teeth) otherwise known as the bite block or occlusal plain. The lower members 12 are of a minimal thickness such that air flow and the oral architecture are minimally impinged but thick enough to allow for the molding of the attachment means (representatively depicted as 16). The attachment means (representatively depicted as 16) may be, in one embodiment, comprised of an attachment means (representatively depicted as 16) for molding in or upon lower member 12 of the oral appliances 11. The attachment means (representatively depicted as 16) are located on what would be the area of the lower members 12 in the area that would be directly above the crown(s) of the tooth (teeth) otherwise known as the bite block or occlusal plain. The attachment means (representatively depicted as 16) is comprised of a recessed cavity and a lip-like area, for retaining attachment element 15 (i.e., the head of the screw). Said lip-like area is formed in a manner whereby even with the application of a force attempting to vertically remove said attachment element 15 from the lower member 12 and area (representatively depicted as 16) the attachment element's will be held fast. Said manner (i.e., the area representatively depicted as 16) for attachment may be effectuated by molding, casting or otherwise effecting said attachment means (representatively depicted as 16) to the lower member 12. Said cavity is further comprised of a large circular opening, a shaft passage way and an oblong distal end, without fear of falling through or out of the member because of the lip-like means. Accordingly, an attachment element's 15 head 52 is inserted into the circular opening whereby it becomes recessed therein. Then only the shaft of the attachment element 15 should be protruding. Accordingly, the attachment element's 15 shaft 55 may then pass through the shaft way to the distal end. Once at the distal end the shaft of the attachment element 15 will have the ability to move laterally without the head 52 becoming dislodged or disarticulated. Accordingly, distal end, by way of insertion into the opening and passage through the shaft way is the means by which the oral appliance 11 is articulated into the correct anatomical position. In turn, the circular opening allows the oral appliance to become disarticulated and removed from the mouth.

In another embodiment of FIG. 1 for the lower 12 member, the areas on the lower 12 member (representatively depicted as 16) would have an attachment means for attachment to the attachment element 72 and therein the attachment element 72 without retaining nut 71, 15. The areas (representatively depicted as 16) are in what would be the area of the lower members 12 that would be directly above the respective crown(s) of the tooth (teeth) otherwise known as the bite block or occlusal plain. The lower members 12 are of a minimal thickness such that air flow and the oral architecture are minimally impinged but thick enough to allow for the molding of the attachment means (representatively depicted as 16). The attachment means (representatively depicted as 16) may be, in one embodiment, comprised of an attachment means (representatively depicted as 16) for molding in or upon lower member 12 of the oral appliances 11. The attachment means (representatively depicted as 16) are located on what would be the area of the lower members 12 in the area that would be directly above the crown(s) of the tooth (teeth) otherwise known as the bite block or occlusal plain. The lower members 12 are of a minimal thickness such that airflow and the oral architecture are minimally impinged but thick enough to allow for the molding of the attachment means (representatively depicted as 16). The attachment means (representatively depicted as 16) is comprised of a recessed cavity and an lip like area, for retaining attachment element 15 (i.e., the head of the screw). Said lip-like area is formed in a manner whereby even with the application of a force attempting to vertically remove said attachment element 15 from the lower member 12 and area (representatively depicted as 16) the attachment element will be held fast. Said manner (i.e., the area representatively depicted as 16) for attachment may be effectuated by molding, casting or otherwise attaching or affixing said attachment means (representatively depicted as 16) to the lower member 12. Said cavity is further comprised of a large circular opening, a shaft passage way and an oblong distal end. Accordingly, an attachment element's 15 head 52 is inserted into the circular opening whereby it becomes recessed therein. Then only the shaft of the attachment element 15 should be protruding. Accordingly, the attachment element's 15 shaft 55 may then pass through the shaft way to the distal end. Once at the distal end the shaft of the attachment element 15 will have the ability to move laterally without the head 52 becoming dislodged or disarticulated. Accordingly, distal end, by way of insertion into the opening and passage through the shaft way is the means by which the oral appliances 11 are articulated into the correct anatomical position for the patient. In turn, the circular opening allows the oral appliance to become disarticulated and removed from the patient's mouth.

In an alternative embodiment FIG. 1 may depict a profile of a custom fitted and manufactured oral appliance 11, or alternatively an appliance that may be mass produced, either embodiment may thereby be constructed of a material capable of withstanding the physical and chemical stresses exerted from placement and usage in the mouth while capable of customization to the user's specific anatomical features, e.g., flexite. In this embodiment, it should be noted that the upper and lower attachment means used are interchangeably—provided that they are on the opposing members. Therein a bi-lateral embodiment is depicted, consisting of upper attachment means 14 that may be cast, molded or affixed by the attending professional or alternatively pre-cast, pre-molded, pre-affixed, attachment elements 15 (representatively identified as 71), and lower attachment means (representatively identified as 16) that may be cast, molded or affixed by the attending professional or alternatively pre-cast, pre-molded, pre-affixed. The attachment means 14, (representatively identified as 16) are on what would be the area of the upper and lower members 13, 12 in the areas that would be directly above or on top of the crown(s) of the tooth (teeth) otherwise known as the bite block or occlusal plain. The upper and lower members 13, 12 are of a minimal thickness such that air flow and the oral architecture are minimally impinged but thick enough to allow for the attachment, molding, casting or insertion of the attachment means (representatively identified as 16). The upper member 13 is molded, custom or otherwise derived, from a maxillary impression. The lower member 12 is molded, custom or otherwise derived, from a mandibular impression. Upper member 13 has an attachment means 14 on both respective adjacent sides of said member. Said attachment means 14 in turn have attachment elements 15 (representatively identified as 71). In turn, lower member 12 has an attachment means (representatively identified as 71) on the respective adjacent sides of said member. Said attachment means (representatively identified as 16) in turn have said attachment elements 15 (representatively identified as 71) connected or attached thereto.

FIG. 2 FIG. 2 depicts a profile of a custom fitted or mass produced oral appliance 21 that is constructed of material capable of withstanding the physical and chemical stresses exerted from placement and usage in the mouth while capable of being customized to the user's specific anatomical features, e.g., flexite. In this diagram, an anterior embodiment 21 with longitudinal attachment means 14, 16, and element 15 is depicted. The attachment means 14, 16 are on what would be the area of the upper and lower members 13, 12 in the area that would be directly above the crown(s) of the tooth (teeth) otherwise known as the bite block or occlusal plain. The upper and lower members 13, 12 are of a minimal thickness such that air flow and the oral architecture are minimally impinged but thick enough to allow for the attachment, molding, or insertion of the attachment means 14, 16. The upper member 13 is molded, custom or otherwise derived, from a maxillary impression. The lower member 12 is molded, custom or otherwise derived, from a mandibular impression. Upper mold 13 has secured thereto an attachment means 14, located anteriorly and oriented longitudinally. Said attachment means in turn has an attachment element 15 connected thereto. In turn, lower member 12 has an attachment means 16, located anteriorly and oriented longitudinally. Said attachment means 16 in turn has an attachment element 15 attached thereto.

In another embodiment of FIG. 2, FIG. 2 depicts a profile of a custom fitted or mass produced oral appliance 21 that is constructed of material that is capable of withstanding the physical and chemical stresses exerted from placement and usage in the mouth while capable of being customized to the user's specific anatomical features, e.g., flexite. In this diagram, an anterior embodiment 21 with longitudinal attachment means (representatively identified as 14 and 16), and element 71 is depicted. The attachment means (representatively identified as 14 and 16) are on what would be the area of the upper and lower members 13, 12 in the area that would be directly above the crown(s) of the tooth (teeth) otherwise known as the bite block or occlusal plain. The upper and lower members 13, 12 are of a minimal thickness such that air flow and the oral architecture are minimally impinged but thick enough to allow for the molding of the attachment means (representatively identified as 14 and 16). The upper member 13 is molded, custom or otherwise derived, from a maxillary impression. The lower member 12 is molded, custom or otherwise derived, from a mandibular impression. Upper mold 13 has molded therein an attachment means (representatively identified as 14), located anteriorly and oriented longitudinally. Said attachment means, in turn, has an attachment element 71 connected thereto. In turn, lower member 12 has an attachment means (representatively identified as 16), located anteriorly and oriented longitudinally. Said attachment means (representatively identified as 16) in turn has an attachment element 71 attached thereto.

The areas on the upper 13 member (representatively depicted as 14) would have an attachment means for attachment to the attachment element 71 with a retaining nut 72 affixed therein. The area (representatively depicted as 14) are in what would be the area of the upper members 13 that would be directly above the respective crown(s) of the tooth (teeth) otherwise known as the bite block or occlusal plain. The upper members 13 are of a minimal thickness such that air flow and the oral architecture are minimally impinged but thick enough to allow for the molding of the attachment means (representatively depicted as 14). The attachment means (representatively depicted as 14) may be, in one embodiment, comprised of an opening and a track-like means in which a recessed retaining nut (i.e., 72) may be located within the track-like means. The nut (i.e., 72) is free to move within the confines of the track but is fixedly connected so that rotation is not possible. The attachment area (representatively depicted as 14) may molded into or on the upper member 13 such that a sound and durable manner of affixation may be obtained.

The areas on the lower 12 member (representatively depicted as 16) would have an attachment means for attachment to the attachment element 15. The areas (representatively depicted as 16) are in what would be the area of the lower members 12 that would be directly above the respective crown(s) of the tooth (teeth) otherwise known as the bite block or occlusal plain. The lower members 12 are of a minimal thickness such that air flow and the oral architecture are minimally impinged but thick enough to allow for the molding of the attachment means (representatively depicted as 16). The attachment means (representatively depicted as 16) may be, in one embodiment, comprised of an attachment means (representatively depicted as 16) for molding in or upon lower member 12 of the oral appliances 21. The attachment means (representatively depicted as 16) are located on what would be the area of the lower members 12 in the area that would be directly above the crown(s) of the tooth (teeth) otherwise known as the bite block or occlusal plain. The lower members 12 are of a minimal thickness such that air flow and the oral architecture are minimally impinged but thick enough to allow for the molding of the attachment means (representatively depicted as 16). The attachment means (representatively depicted as 16) is comprised of a recessed cavity and an lip like area, for retaining attachment element 15 (i.e., the head of the screw). Said lip-like area is formed in a manner whereby even with the application of a force attempting to vertically remove said attachment element 15 from the lower member 12 and area (representatively depicted as 16) the attachment element will be held fast. Said manner (i.e., the area representatively depicted as 16) for attachment may be effectuated by molding, casting or otherwise attaching or affixing said attachment means (representatively depicted as 16) to the lower member 12. Said cavity is further comprised of a large circular opening, a shaft passage way and an oblong distal end. Accordingly, an attachment element's 15 head 52 is inserted into the circular opening whereby it becomes recessed therein. Then only the shaft of the attachment element 15 should be protruding. Accordingly, the attachment element's 15 shaft 55 may then pass through the shaft way to the distal end. Once at the distal end the shaft of the attachment element 15 will have the ability to move laterally without the head 52 becoming dislodged or disarticulated. Accordingly, distal end, by way of insertion into the opening and passage through the shaft way is the means by which the oral appliances 21 are articulated into the correct anatomical position for the patient. In turn, the circular opening allows the oral appliance to become disarticulated and removed from the patient's mouth.

FIG. 3 FIG. 3 depicts one possible attachment element 15 along with retaining nut 72, forming assembly 71. The attachment element 15 may be comprised of a head 52, shaft 53, area 54, region 55 appropriately threaded and a distal end 51. Distal end 51 may designed to accept a flat, Phillips, or Allen type screw head adjustment means. The attachment element 15 should be constructed of titanium or other similar metal, composition or composite of similar structural integrity and strength. The head 52 of the attachment element 15 may have a manner by which the attachment element 15 is put into place on the upper member 13 of the oral device 11 (or 21). The shaft may be smooth (not shown) or threaded 55 or a varying combination thereof, but must be of a nature that allows for attachment into the upper attachment means 14 of the oral appliance. The attachment element 15 may be of a length of between 0.010" and 0.250" and preferably between 0.100" and 0.200" in length. The head 52 of the attachment element may be of a diameter of between 0.175 and 0.100" with around 0.150" being the preferred diameter. The head 52 may range in thickness between 0.010" and 0.050" with around 0.030" being preferred. The shaft 55 may be threaded or otherwise adapted. The shaft may consists of two areas, one threaded and one non-threaded (not shown). Said area 55 may be of a length between 0.010" and 0.215" with 0.170" being preferred and have a circumference of between 0.090" and 0.070" but should be between 0.080" and 0.089". Said retaining nut 72 is free to move along the confines of the track-like means 133 of attachment means 14, but is prevented from rotating or dislodging. Said retaining nut 72 must mate, through threading of hole 73, with the threading of shaft 55 and be of appropriate size to be retained by attachment means 14.

FIG. 4 FIG. 4 depicts an attachment means 16 for placement in, upon or by other means affix to the lower member 12 of the oral appliances 11, 21. The attachment means 16 are located on what would be the area of the lower members 12 in the area that would be directly above the crown(s) of the tooth (teeth) otherwise known as the bite block or occlusal plain. The lower members 12 are of a minimal thickness such that air flow and the oral architecture are minimally impinged but thick enough to allow for the attachment, molding, or insertion of the attachment means 16. The attachment means 16 is comprised of a cavity 92 and an encompassing mass 93. Said mass 93 is attached to the lower mold 12 in a manner by which upon the application of a force attempting to remove said attachment means 16 from the lower member 12 it will hold fast. Said manner for attachment may be effectuated by molding, casting, welding, bolting or otherwise attaching or affixing said attachment means 16 to the lower member 12. Said cavity 92 is further comprised of a large circular opening 91, a shaft way 94, and an oblong distal end 95. Accordingly, an attachment element's head 52 is inserted into the circular opening 91 whereby it becomes recessed therein. Then only the shaft of the attachment element 15 should be protruding. Accordingly, the attachment element's shaft 55 may then pass through the shaft way 94 to the distal end 95. Once at the distal end 95 the shaft of the attachment element 15 will have the ability to move laterally without the head 52 becoming dislodged or disarticulated. Accordingly, distal end 51, by way of insertion into the opening 91 and passage through the shaft way 94 is the means by which the oral appliances 11 and 21 are articulated into the correct anatomical position for the patient. In turn, the circular opening 91 allows the oral appliance to become disarticulated and removed from the patient's mouth.

FIG. 5 FIG. 5 depicts a view of the invention's lower bilateral and anterior longitudinally oriented attachment means 16 with a screw overlay 101. Said screw overlay 101 depicts the path of the attachment element(s) 15, 42 as it traverses through opening 91, shaft way 94, and oblong end 95 of attachment means 16.

FIG. 6 FIG. 6 depicts an attachment means for placement in, upon or by other means affix to the lower member 12 of the oral appliance. The attachment means are located on what would be the area of the lower members 12 in the areas that would be directly above the crown(s) of the tooth (teeth) otherwise known as the bite block or occlusal plain. The lower members 12 are of a minimal thickness such that air flow and the oral architecture are minimally impinged but thick enough to allow for the attachment, molding, or insertion of the attachment means. The attachment means is comprised of a cavity 111 and an encompassing mass 112. Said mass 112 is attached to the lower mold 12 in a manner by which upon the application of a force attempting to remove said attachment means from the lower member 12 it will hold fast. Said manner for attachment may be effectuated by molding, casting welding, bolting or otherwise attaching or affixing said attachment means to the lower member 12. An attachment element's head 52 is inserted into the cavity where it becomes recessed therein. Alternatively, in other embodiments, an attachment element's head is permanently inserted into cavity 73 whereby is becomes recessed therein, forming a "one piece" appliance. Then only the shaft of the attachment element 15 (or 42) should be protruding therefrom.

FIG. 7 FIG. 7 depicts a view of the invention's lower anteriorly located, latitudinally oriented attachment means with a screw overlay 121. Said screw overlay 121 depicts the path of the attachment element(s) 15, 42 as it traverses through cavity 111 of attachment means.

FIG. 8 FIG. 8 depicts an attachment means 14 for secure placement in the upper member 13 of the oral appliance. The attachment means 14 are on what would be the area of the upper members 13 in the area that would be directly above the crown(s) of the tooth (teeth) otherwise known as the bite block or occlusal plain. The upper members 13 are of a minimal thickness such that air flow and the oral architecture are minimally impinged but thick enough to allow for the attachment, molding, or insertion of the attachment means 14. The attachment means 14 is comprised of an opening 133 and a track-like means 132 and recessed retaining nut 72 which is fixedly attached to attachment element 15. Attachment element 15 is visually superimposed over retaining nut 72. Nut 72 is free to move within the confines of track 132, but is fixedly connected so that rotation is not possible. The attachment means 14 may be cast, molded or otherwise inserted and or attached into or to said upper member 13 allowing for a sound and durable manner of affixation. The length of the attachment means 14 may be between 0.300" to 0.900"; with between 0.500" and 0.700" being preferable.

FIG. 9 FIG. 9 depicts a side profile of attachment means 14 with retaining nut 72 visually superimposed therein and attachment element 15. The thickness 141 of the attachment means 14 may be between 0.100" and 0.010"; with between 0.050" and 0.080" being preferable. In an embodiment having a thickness of 0.080", lip 131 has a thickness of 0.030" and wall 142 has a height of 0.050". The attachment means 14 should be constructed of titanium or other similar metal, composition or composite of similar structural integrity and strength.

FIG. 10 FIG. 10 depicts, attachment means 14 with attachment element 15 removed. Within confines of track like means 132 and aligned with hole 133 of said attachment element 14 is retaining nut 72. Within said retaining nut 72 is hole 73. Hole 73 is threaded or otherwise adapted to accept shaft 55 of attachment element 15. Said retaining nut 72 is free to move along the confines of track like means 132, however, said track's 132 width is truncated by lips 131, preventing rotation of said retaining nut 72.

FIG. 11 FIG. 11 depicts the upper member 161 used in a bi-lateral attachment means 14, 16 embodiment. Upper mold 13 of the oral appliance 11 has the attachment means 14 secured thereto. Said upper mold 13 is custom molded and then fitted to a patient and is preferably constructed of flexite or a material capable of maintaining structural integrity, rigidity and form throughout use while capable of being customized to the user's specific anatomical features.

FIG. 12 FIG. 12 depicts the lower member 171 used in a bi-lateral attachment means 14, 16 embodiment. Lower mold 12 of the oral appliance 11 has the attachment means 16 secured thereto. Said lower mold 12 is custom molded and then fitted to a patient and is preferably constructed of flexite or a material capable of maintaining structural integrity, rigidity and form throughout use while capable of being customized to the user's specific anatomical features.

FIG. 13 FIG. 13 depicts the upper member 181 used in an anteriorly located, longitudinally oriented attachment means 14, 16 embodiment. Upper mold 13 of the oral appliance 21 has the attachment means 14 secured thereto. Said upper mold 13 is custom molded and then fitted to a patient and is preferably constructed of flexite or a material capable of maintaining structural integrity, rigidity and form throughout use while capable of being customized to the user's specific anatomical features.

FIG. 14 FIG. 14 depicts the lower member 191 used in an anteriorly located, longitudinally oriented attachment means 14, 33 embodiment. Lower mold 12 of the oral appliance 21 has the attachment means 16 secured thereto. Said lower mold 12 is custom molded and then fitted to a patient and is preferably constructed of flexite or a material capable of maintaining structural integrity, rigidity and form throughout use while capable of being customized to the user's specific anatomical features.

FIG. 15 FIG. 15 depicts the upper member 201 used in an anteriorly located, latitudinally oriented attachment means and 14 embodiment. Said upper mold 13 is custom molded and then fitted to a patient and is preferably constructed of flexite or a material capable of maintaining structural integrity, rigidity and form throughout use while capable of being customized to the user's specific anatomical features.

FIG. 16 FIG. 16 depicts the lower member 211 used in an anteriorly located, latitudinally oriented attachment means and 14 embodiment. Lower mold 12 of the oral appliance has the attachment means 14 secured thereto. Said lower mold 12 is custom molded and then fitted to a patient and is preferably constructed of flexite or a material capable of maintaining structural integrity, rigidity and form throughout use while capable of being customized to the user's specific anatomical features.

FIG. 17 FIG. 17 depicts a longitudinal cross section of upper attachment means 14 articulated with lower attachment means 16. Attachment element 15, with its flat distal end 51 is engaged in the oblong opening 95 of lower attachment means 16. The oblong opening 95 at end of track 92 allows for lateral mandible movement. Articulation is possible whereby flat distal end 52 is inserted into aforementioned opening 91. Area 54 may be a lock washer or may comprise one and the same pieces of metal as element 15. Thus area 54, either permanently affixed, i.e. milled or screwed on, should be preferably of width 0.125" and thickness of 0.04", prevents vertical advancement of attachment element 15, thereby allowing threading 55, preferably of density 28 threads per inch, on said element 15 to mate and tighten with recessed nut 72, hence fixing attachment element 15 within a determined position within hole 73 of track 133. Nut 72 is recessed and fastened to attachment means 14 in a manner that prevents rotation, but allows longitudinal movement along the confines of the track 133.

What I claim is:

1. An intra-oral dental appliance to be inserted into the oral cavity of a human being for treatment of sleep apnea, snoring, bruxism, and temporo-mandibular joint disorder, said dental appliance comprising: a molded member, said molded member comprising a bi-lateral under surface, conforming to the clinical occlusal plane of a human being, further conforming to the maxillary dentition and a second molded member, said second molded member further comprising a bi-lateral upper surface, conforming to the clinical occlusal plane of a human being, further conforming to the mandibular dentition; with a first attachment means securable to said bi-lateral under surface; with a second attachment means securable to said bi-lateral upper surface; at least one attachment element whereby said attachment element comprises means whereby said attachment element may be connected or attached to said first attachment means and may be further connected or attached to said second attachment means.

2. An intra-oral dental appliance for treatment of sleep apnea, snoring, bruxism, and temporo-mandibular joint disorder, said dental appliance comprising:

(a) a first rigid structural shell having a custom molded upper member conforming to the patient's maxillary dentition, said first rigid structural shell having an under surface parallel to said patient's clinical occlusal plane, and a second rigid structural shell having a custom molded lower member conforming to the patient's mandibular dentition, said second rigid structural shell having an upper surface parallel to said patient's clinical occlusal plane;

(b) with at least one first attachment means securable to the anterior of said under surface, whereas said first attachment means is oriented latitudinally on said first rigid structural shell;

(c) with at least one second attachment means securable to the anterior of said upper surface whereas said second attachment means is oriented latitudinally on said second rigid structural shell;

(d) an affixing means connected to said first attachment means to allow securable attachment of said first attachment means to said under surface of said first rigid structural shell;

(e) an affixing means connected to said second attachment means to allow securable attachment of said second attachment means to said upper surface of said second rigid structural shell; and (f) an attachment element capable of connecting said first attachment means and said second attachment means.

3. An appliance according to claim 2 manufactured of a material capable of withstanding the chemical and physical stresses resulting from being inserted into the mouth of a human being.

4. An appliance according to claim 2 that further comprises a means for the insertion and securement thereto of said attachment element further facilitating the connection of said first rigid structural shell and said second rigid structural shell.

5. An appliance according to claim 2 that further comprises a means for the insertion and securement thereto of said attachment element further facilitating the connection of said first rigid structural shell and said second rigid structural shell.

6. An appliance means according to claim 2 connected to said first attachment means to allow securable attachment of said first attachment means to said under surface of said first structural shell.

7. A intra-oral appliance, said appliance adapted to be disposed within the oral cavity, used for the treatment of sleep apnea, snoring, bruxism, temporo-mandibular joint disorder, upper airway resistance syndrome, sleep disordered breathing, chronic fatigue syndrome, asthma, fibromyalgia, diabetes, hypertension, headache, gastroesophogeal reflux disease ("GERD") aka heartburn, and/or tinnitus, said appliance comprising: a first molded member, said first molded member having a bi-lateral under surface parallel to the clinical occlusal plane within said oral cavity, further conforming to a maxillary dentition and a second molded member, said second molded member comprising a bi-lateral upper surface parallel to the clinical occlusal plane within said oral cavity, further conforming to a mandibular dentition; with a first attachment element securable to said bi-lateral under surface; with a second attachment element securable to said bi-lateral upper surface; an attachment means connected or attached to said first attachment element further adjustably attached to said secured second attachment element.

8. An infinitely adjustable intra-oral dental appliance, said appliance disposed within the oral cavity, said appliance comprising: a first molded member, said first molded member having a bi-lateral under surface conforming to the clinical occlusal plane within said oral cavity, conforming to a maxillary dentition and a second molded member, said second molded member comprising a bi-lateral upper surface conforming to the clinical occlusal plane within said oral cavity, conforming to a mandibular dentition; with at least one first attachment means securable to said bi-lateral under surface; with at least one second attachment means securable to the bi-lateral upper surface; at least one attachment element that may be connected or attached to said first attachment means whereby said attachment element further comprises a means whereby said attachment element may be positioned or adjustably attached to said second attachment element.

9. An intra-oral appliance according to claim 8 whereby said infinite adjustability is determined by the dimensions of said oral cavity into which said appliance is to be inserted.

10. An intra-oral appliance according to claim 8 whereby said first attachment means further comprises a means for the insertion of said attachment element and its positioning and securement therein.

11. An intra-oral appliance according to claim 8 whereby said second attachment means further comprises a means for the insertion of said attachment element and its positioning therein.

12. A intra-oral appliance according to claim 8 whereby said first attachment means further comprises a threaded member and a mating member for insertion and securement of said attachment element into said first attachment means.

13. An intra-oral appliance according to claim 8 whereby said second attachment means provides for the insertion and retention of said attachment element into said second attachment means.

14. An intra-oral appliance according to claim 8 whereby said second attachment means allows for the movement of said attachment element while retained therein.

15. An intra-oral appliance according to claim 8 whereby said attachment element may be customly positioned and affixed within said first attachment means and further provide for the insertion of said attachment element into said second attachment means.

16. An intra-oral appliance according to claim 8 whereby said first attachment means allows for the infinite adjustability and positioning of said attachment element within the confines and dimensions of said oral cavity.

* * * * *